(12) United States Patent
Thanigachalam et al.

(10) Patent No.: US 7,805,992 B2
(45) Date of Patent: Oct. 5, 2010

(54) GAS SENSOR HOUSING FOR USE IN HIGH TEMPERATURE GAS ENVIRONMENTS

(75) Inventors: Palani Thanigachalam, Bangalore (IN); Saju Ramachandran, Bangalore (IN); Ramsesh Anilkumar, Bangalore (IN)

(73) Assignee: Honeywell International Inc., Morristown, NJ (US)

( * ) Notice: Subject to any disclaimer, the term of this patent is extended or adjusted under 35 U.S.C. 154(b) by 631 days.

(21) Appl. No.: 11/729,129

(22) Filed: Mar. 27, 2007

(65) Prior Publication Data

US 2008/0236246 A1 Oct. 2, 2008

(51) Int. Cl.
*G01D 11/24* (2006.01)

(52) U.S. Cl. ......................................................... 73/431

(58) Field of Classification Search ....... 73/23.2–31.07, 73/431
See application file for complete search history.

(56) References Cited

U.S. PATENT DOCUMENTS

| | | | |
|---|---|---|---|
| 4,277,323 A | 7/1981 | Muller et al. ............. 204/195 S |
| 4,282,080 A | 8/1981 | Muller et al. ............. 204/195 S |
| 4,283,261 A | 8/1981 | Maurer et al. ............. 204/195 S |
| 4,300,990 A | 11/1981 | Maurer .................... 204/195 S |
| 4,305,803 A | 12/1981 | Beyer et al. .............. 204/195 S |
| 4,310,401 A | 1/1982 | Stahl ....................... 204/195 S |
| 4,368,431 A | 1/1983 | Rohr et al. ................ 324/464 |
| 4,419,212 A | 12/1983 | Dietz et al. ................ 204/424 |
| 4,437,971 A | 3/1984 | Csanitz et al. ............. 204/427 |
| 4,489,596 A | 12/1984 | Linder et al. ................ 73/116 |
| 4,556,475 A | 12/1985 | Bayha et al. ................ 204/427 |
| 4,560,463 A | 12/1985 | Frey et al. .................. 204/424 |
| 4,609,454 A | 9/1986 | Ziegler ...................... 204/427 |
| 4,636,293 A | 1/1987 | Bayha et al. ................ 204/428 |
| 4,736,618 A | 4/1988 | Usami et al. ................ 73/31.05 |
| 4,756,885 A | 7/1988 | Raff et al. ..................... 422/98 |
| 5,246,562 A | 9/1993 | Weyl et al. ................. 204/424 |
| 5,625,156 A * | 4/1997 | Serrels et al. ............ 73/863.51 |
| 5,942,092 A | 8/1999 | Weyl et al. ................. 204/424 |
| 5,955,656 A | 9/1999 | Graser et al. ............... 73/23.31 |
| 6,018,982 A | 2/2000 | Friese et al. ................ 73/23.2 |
| 6,164,120 A | 12/2000 | Friese et al. ................ 73/23.2 |
| 6,206,377 B1 | 3/2001 | Weyl .......................... 277/317 |
| 6,223,583 B1 | 5/2001 | Friese et al. ............... 73/23.31 |
| 6,273,432 B1 | 8/2001 | Weyl et al. .................. 277/591 |
| 6,311,453 B1 | 11/2001 | Mechnick .................. 52/749.1 |
| 6,319,376 B1 | 11/2001 | Graser et al. ............... 204/424 |

(Continued)

FOREIGN PATENT DOCUMENTS

GB 2166866 A 5/1986

(Continued)

*Primary Examiner*—Hezron Williams
*Assistant Examiner*—Tamiko D Bellamy

(57) ABSTRACT

An apparatus and method for packaging and operating a gas sensor for use in high temperature gas environments. A gas sensor can be configured, which includes a sensor element and a housing in which the sensor element is located. A parallel gas path can be configured form said housing, wherein said parallel gas path is based on the natural differential pressure with respect to the velocity of said gas. The parallel gas path is preferably vertical to provide a sufficient friction to soot particles compared to the gas, such that when a partial quantity of said gas reaches said sensor element, said soot particles are avoided by said sensor element.

14 Claims, 4 Drawing Sheets

U.S. PATENT DOCUMENTS

| | | | |
|---|---|---|---|
| 6,344,134 B1 | 2/2002 | Yamada et al. | 205/781 |
| 6,347,543 B1 | 2/2002 | Geier et al. | 73/23.31 |
| 6,352,632 B1 | 3/2002 | Inagaki et al. | 204/425 |
| 6,375,828 B2 | 4/2002 | Ando et al. | 205/781 |
| 6,408,680 B2 | 6/2002 | Friese et al. | 73/23.31 |
| 6,432,288 B1 * | 8/2002 | Nielsen et al. | 204/424 |
| 6,474,655 B1 | 11/2002 | Weyl et al. | 277/650 |
| 6,487,890 B1 | 12/2002 | Weyl et al. | 73/23.31 |
| 6,527,573 B2 | 3/2003 | Stein, Sr. et al. | 439/260 |
| 6,585,872 B2 | 7/2003 | Donelon et al. | 204/424 |
| 6,613,206 B1 | 9/2003 | Weyl et al. | 204/424 |
| 6,672,132 B1 | 1/2004 | Weyl et al. | 73/23.31 |
| 6,766,817 B2 | 7/2004 | da Silva | 137/1 |
| 6,918,404 B2 | 7/2005 | Dias da Silva | 137/132 |
| 7,066,586 B2 | 6/2006 | da Silva | 347/85 |
| 2002/0048991 A1 | 4/2002 | France et al. | 439/587 |
| 2003/0160844 A1 | 8/2003 | da Silva | 347/84 |
| 2004/0077201 A1 | 4/2004 | Kobayashi et al. | 439/190 |
| 2004/0159547 A1 | 8/2004 | Haraguchi et al. | 204/424 |
| 2004/0187919 A1 | 9/2004 | da Silva | 137/1 |
| 2004/0196338 A1 | 10/2004 | da Silva | 347/85 |
| 2004/0237529 A1 | 12/2004 | da Silva | 60/721 |
| 2005/0160840 A1 * | 7/2005 | Allmendinger | 73/863.51 |

FOREIGN PATENT DOCUMENTS

| | | |
|---|---|---|
| GB | 2289944 A | 12/1995 |
| JP | 05052143 A * | 3/1993 |

* cited by examiner

GAS SENSOR HOUSING FOR USE IN HIGH TEMPERATURE GAS ENVIRONMENTS

TECHNICAL FIELD

Embodiments are generally related to gas sensors. Embodiments are also related to sensor housing systems and methods. Embodiments are additionally related to gas sensor housings for use in high temperature gas environments.

BACKGROUND OF THE INVENTION

Many different types of gas sensor housings or units have been implemented in environments containing corrosive gases. In this type of situation, the gas sensor housing can be operatively connected to a central station to form a gas sensing signaling system or device. In the context of automotive exhaust gas applications, in order to reduce the automotive emission levels it is of prime importance to measure the constituents of exhaust gas (e.g., NOx, $So_2$, CO, $CO_2$, etc). In industrial applications, the ability to monitor and detect gas is also of primary importance.

In order to protect industrial plants or installations, pipe conduit channels, chemical storage areas and so forth, against fires and also to prevent humans from being exposed to toxic gases, it is desirable to detect at an incipient stage, dangerous concentrations of combustible or noxious gases. In response to such detection, it is then possible to initiate suitable counter measures, for instance shutting down operating installations, which are improperly functioning, closing off leaking pipe conduits, starting ventilators or other exhaust apparatus, opening emergency exits and otherwise signaling the occupants or personnel of the need to leave the area. In this manner fires, explosions, toxic effects and other damage may be prevented. Thus, In order to detect undesired and dangerous concentrations of oxidizable or combustible gases, gas sensing signaling or alarm systems composed of gas sensing units can be implemented, which are connected with a central station.

A typical gas sensing unit contains a gas sensor which, when exposed to the action of reducible gases, alters its electrical resistance. In terms of physical construction, electrochemical gas sensors usually include some type of external housing, which acts as a reservoir for an electrolyte. A wick may be utilized to keep the electrolyte in contact with the electrodes. External electrical terminals are also often provided, which make electrical contact with the electrodes. Many commercially available gas sensors are of the amperometric type having two or more electrodes in which a catalytically active metal is fixed to a porous substrate.

In one prior art gas sensor design, a planar sensing element can be immobilized in gas-tight fashion, by way of a sealing element, and implemented in a pass-through component of an exhaust-gas-side lower ceramic shaped element. The exhaust-gas-side ceramic shaped element can possess, on the end surface and facing away from the exhaust gas, a recess that surrounds the pass-through and into which a glass seal is introduced. A further ceramic shaped element is then joined via a metal solder join to the housing on the glass seal. The glass seal encloses the sensing element inside the recess, and constitutes a gas-tight join between ceramic shaped element and sensing element at this point. One of the problems with this type of gas sensor configurations is that the effect of high temperatures causes errors in the functionality of the sensor system.

Another type of gas sensor configuration includes the use of a sensor element that is fixed in a tubular, metallic housing in a gas-tight manner. At its lower part, the tubular housing contains a lip facing radially outward and which forms a sealing flange. Such a gas sensor can be mounted in an opening of an exhaust system, with the lip sitting on a sealing seat formed in the opening. A banjo bolt can be led over the housing and screwed into a thread arranged in the opening, thereby joining the lip to the exhaust system in a gas-tight manner. Problematic in this design is, however, that the pressing or upsetting of the relatively thin-walled material of the housing can produce micro-cracks at the lip, which can cause the housing to leak.

$O_2$ (oxygen), $NO_x$ (nitrogen oxide), $NH_3$ (ammonia), $SO_x$ (sulphur oxide), CO (carbon monoxide) and $CO_2$ (carbon dioxide) sensors are used in automotive exhaust gas pipes in most gasoline and diesel engines to control pollution and improve combustion performance. Exhaust gas contains soot particles and unburned carbon, which can damage the sensors and erode the sensor element. The sensing element of such sensors can be exposed to a very high temperature of the exhaust gas (excess of 500 C). The sensing element utilized in such sensors may also be directly exposed to high flow velocity of the exhaust gas . . . Prior art sensors, however, do not achieve such parameters.

Prior art sensors are subject over a period of time to errors that can increase due to drift, etc. Additionally, at the temperatures described above, such sensors degrade rapidly. Based on the foregoing, it can be appreciated that designing gas sensors to function at these temperatures is a precise and costly endeavor. Hence to overcome the effect of soot and high temperature, an innovative packaging concept is proposed as described in greater detail herein.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved sensor system and methods.

It is another aspect of the present invention to provide for an improved sensor housing method.

It is a further aspect of the present invention to provide for a better gas sensor housing for use in high temperature gas environments.

The aforementioned aspects and other objectives and advantages can now be achieved as described herein. An apparatus and method for packaging and operating a gas sensor for use in high temperature gas environments are disclosed. A gas sensor can be configured, which include a sensor element and a housing in which the sensor element is located. A parallel gas path can be configured form the housing, wherein the parallel gas path is based on the natural differential pressure with respect to the velocity of the gas. The parallel gas path is preferably vertical to provide a sufficient friction to soot particles compared to the gas, such that when a partial quantity of the gas reaches the sensor element, the soot particles are avoided by the sensor element.

A plurality of fins can be configured from the housing, wherein during an operation of the gas sensor, the temperature of the gas is reduced by providing cooling of the gas through the plurality of fins, thereby improving a performance and a life of the gas sensor, thereby permitting the sensor element to function as a lower temperature sensor element for high temperature applications.

The sensor element can be housed in the parallel gas path, which is located sufficiently away from a main exhaust gas stream. To achieve the parallel flow path, the natural draft differential pressure due to the velocity of gas can be established with a suitable packaging design. This path is preferably vertical in order provide sufficient friction to the dense particles (e.g., soot) compared to gas. Hence, when a partial quantity of gas reaches the sensor element, soot particles can be avoided. Also, during this long travel path, the temperature of the gas can be reduced due to the fins located on the sensor housing which are exposed to air flow. The gas sensor can be designed such that the temperature of the gas under steady state will be approximately 300° C. to 400° C., when main stream exhaust gas temperature is around 900° C. Such features assist in providing a stable, low cost, reliable gas sensor for high-temperature exhaust gas environments.

The gas sensor system disclosed herein can thus be utilized to measure the concentration level of the constituents of an exhaust gas and feed the levels back as feedback to a central station.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
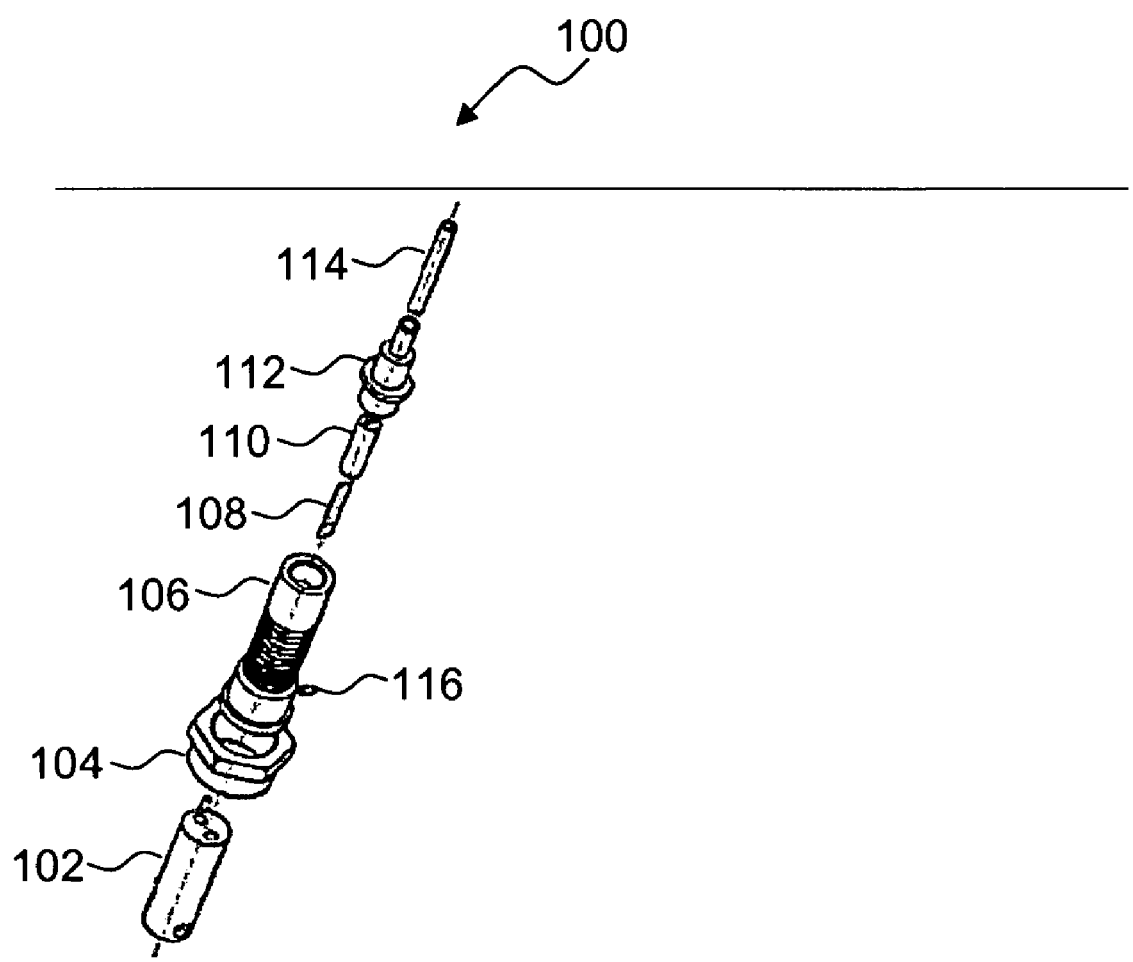
FIG. 1 illustrates a perspective view of a gas sensor housing for use in high temperature gas environments, which can be implemented in accordance with a preferred embodiment.

Referring now to the drawings and in particular to FIG. 1, a perspective view of a gas sensor 100 for use in high temperature gas environments is illustrated, in accordance with a preferred embodiment. The sensor 100 includes a by-pass tube 102 formed from, for expel, SS (Stainless Steel) material. A hex nut 104 can also be provided and formed from an SS material. The gas sensor 100 includes a finned housing 106, which can also be formed from an SS material. Gas sensor 100 also includes a sensor element 108 formed from a ceramic material. A ceramic tube 110 and/or potting in ceramic with a specific AR (activity ratio) can also form a part of gas sensor 100. A sensor holder 112 formed from an SS material can also be provided as a part of gas sensor 100. Additionally, a cable guide 114 formed from Teflon can also form part of gas sensor 100. The gas sensor 100 also includes a dowel 116, which can be formed from an SS material. Additionally the dowell pin 116 can be used to orient the by-pass tube 102 in the direction of flow path, ensuring the flow inlet faces the flow path. A four core cable can also be provided to form an electrical connection with the sensing element 108.

Figure 2:
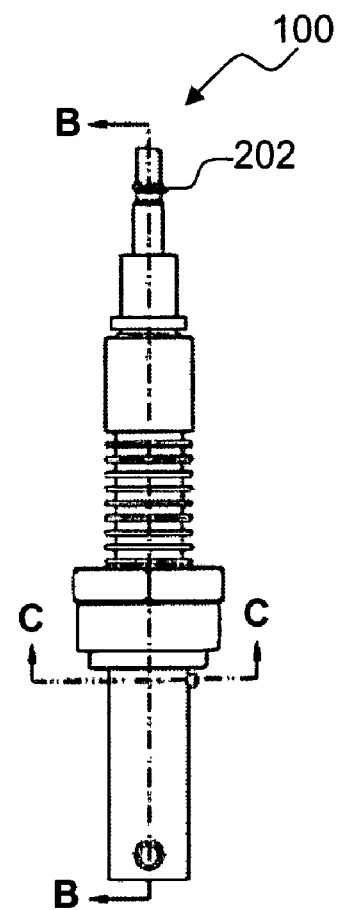
FIG. 2 illustrates a side view of a gas sensor housing depicted in FIG. 1 for use in high temperature gas environments, in accordance with a preferred embodiment.

FIG. 2 illustrates a side view of the gas sensor 100 for use in high temperature gas environments, in accordance with a preferred embodiment. Note that as indicated in FIG. 2, a double crimping with an "O" ring 202 is shown in the side view of the gas sensor 100. Note that in FIGS. 1-5, identical or similar parts or elements are indicated by identical reference numerals. The sensor 100 includes a by-pass tube 102 formed from an MS (mild steel) material. A hex nut 104 can also be provided and formed from an SS material. The gas sensor 100 includes a finned housing 106, which can also be formed from an MS material. Gas sensor 100 also includes a sensor element 108 formed from a ceramic material. A ceramic tube 110 and/or potting in ceramic with a specific AR (activity ratio) can also form a part of gas sensor 100. A sensor holder 112 formed from an SS material that includes a double crimping with an "O" ring 202 can also be provided as a part of gas sensor 100. Additionally, a cable guide 114 formed from Teflon can also form part of gas sensor 100. The gas sensor 100 also includes a dowel 116, which can be formed from an SS material. Four core cables may also be provided to implement an electrical connection with the sensing element 108. Additionally, the dowell Pin 116 can be utilized to orient the by-pass tube 102 in the direction of the flow path, thereby ensuring that the flow inlet faces the flow path.

Figure 3:
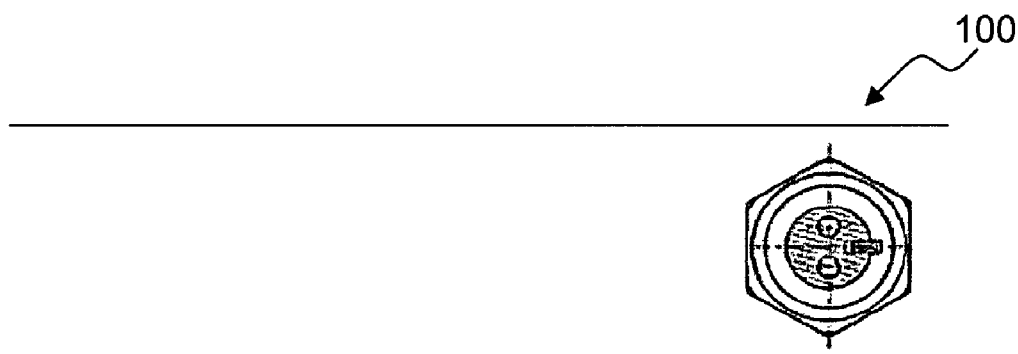
FIG. 3 illustrates a top view C-C of a gas sensor housing for use in high temperature gas environments, which can be implemented in accordance with a preferred embodiment.

FIG. 3 illustrates a top view C-C of the gas sensor 100 depicted in FIGS. 1-2 for use in high temperature gas environments, which can be implemented in accordance with a preferred embodiment. The gas sensor 100 includes a finned housing 106, which can also be formed from an SS material. Gas sensor 100 also includes a sensor element 108 formed from a ceramic material. A ceramic tube 110 and/or potting in ceramic with a specific AR (activity ratio) can also form a part of gas sensor 100. A sensor holder 112 formed from an SS material can also be provided as a part of gas sensor 100. Additionally, a cable guide 114 formed from Teflon can also form part of gas sensor 100. The gas sensor 100 also includes a dowel 116, which can be formed from an SS material. Four core cables may also be provided to form an electrical connection with the sensing element 108. Additionally the dowell Pin 116 can be used to orient the by-pass tube 102 in the direction of the flow path, thereby ensuring that the flow inlet faces the flow path.

Figure 4:
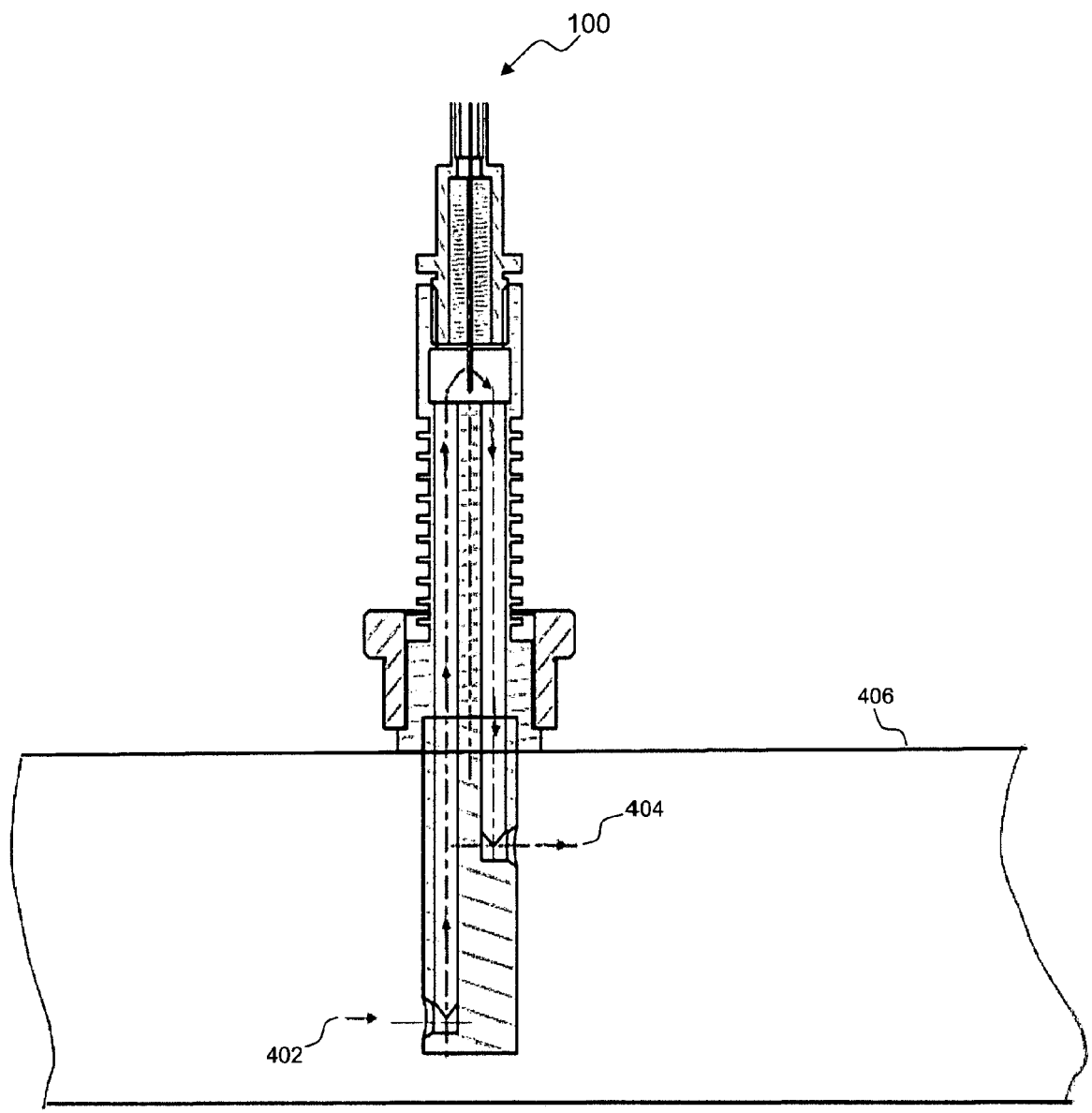
FIG. 4 illustrates a side sectional view B-B of a gas sensor housing for use in high temperature gas environments, which can be implemented in accordance with a preferred embodiment.

FIG. 4 illustrates a side sectional B-B view of the gas sensor 100 depicted in FIGS. 1, 2 and 3 for use in high temperature gas environments, in accordance with a preferred embodiment. A weld is shown in the sectional view B-B of gas sensor 100 depicted in FIG. 4. The gas sensor 100 includes a finned housing 106, which can also be formed from an SS material. Gas sensor 100 also includes a sensor element 108 formed from a ceramic material. A ceramic tube 110 and/or potting in ceramic with a specific AR (activity ratio) can also form a part of gas sensor 100. A sensor holder 112 formed from an SS material can also be provided as a part of gas sensor 100. Additionally, a cable guide 114 formed from Teflon can also form part of gas sensor 100. The gas sensor 100 also includes a dowel 116, which can be formed from an MS material. Four core cables can also be provided to form an electrical connection with the sensing element 108. Additionally the dowell pin 116 can be used to orient the by-pass tube 102 in the direction of the flow path, thereby ensuring that the flow inlet faces the flow path. The gas in-let 402, gas out-let 404 and the exhaust pipe 406 is shown in the gas sensor 100 as the path of gas flow.

Figure 5:
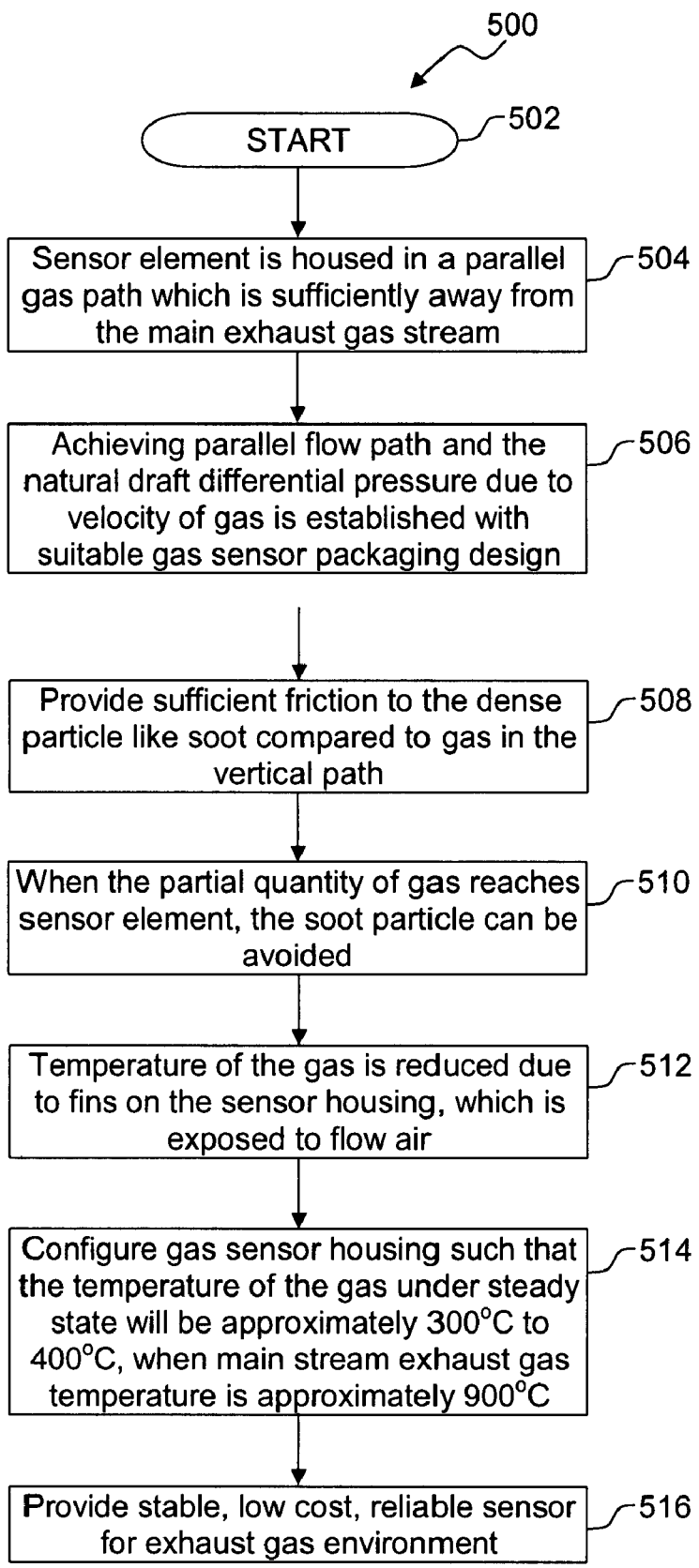
FIG. 5 illustrates a high-level flow chart of operations depicting logical operational steps of gas sensor housing for use in high temperature gas environments, in accordance with a preferred embodiment.

FIG. 5 illustrates a high-level flow chart of operations depicting logical operational steps of a method 500 of configuring and operating the gas sensor 100 for use in high temperature gas environments, in accordance with a preferred embodiment. As depicted at block 502, the process begins. Next, as indicated at block 504, a sensor element 108 can be housed in a parallel gas path 106, which is sufficiently located away from the main exhaust gas stream. Thereafter, as described at block 506, for achieving the parallel flow path, the natural draft differential pressure due to the velocity of gas can be established. Next, as indicated at block 508, a sufficient friction can be provided to dense particles (e.g., soot) as compared to gas in the vertical path.

Thereafter, as depicted at block 510 when the partial quantity of gas reaches the sensor element 108 the soot particle can be avoided. Next, as described at block 512, temperature of the gas can be reduced due to fins 106 on the sensor housing which is exposed to flow air during the long run. Next as depicted at block 514, the gas sensor housing 106 can be designed such that the temperature of the gas under steady state can be approximately 300° C. to 400° C., when a main stream exhaust gas temperature is approximately 900° C. Finally, as indicated at block 516, the stable, low cost, reliable gas sensor 100 for exhaust gas environments can be finally configured and ready to use.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method of detecting a parameter of a gas flowing through a flow channel with a gas sensor, the method comprising:
    providing a housing defining a chamber;
    positioning a gas sensor element in said chamber, the gas sensor element configured to detect a parameter of a gas;
    providing a parallel gas path in said housing, wherein said parallel gas path fluidly couples said chamber to said flow channel, wherein a flow of gas through said parallel gas path is based on a pressure differential cause by a velocity of said gas in said flow channel, wherein said parallel gas path extends away from the flow channel for a distance to provide a sufficient friction to soot particles compared to said gas, such that when a partial quantity of said gas reaches said gas sensor element, said soot particles are substantially avoided by said gas sensor element; and
    disposing a plurality of fins on an outer surface of said housing along said parallel gas path, wherein the plurality of fins are configured to reduce a temperature of said gas flowing through said parallel gas path.

2. The method of claim 1 further comprising:
    exposing said plurality of fins to air to reduce said temperature of said gas flowing through said parallel gas path.

3. The method of claim 1 further comprising;
    configuring said housing to permit said temperature of said gas at said gas sensor element under a steady state to be approximately in a range of 300° C. to 400° C.

4. The method of claim 3 wherein said gas passing through the flow channel is at a temperature of approximately 900° C.

5. The method of claim 1 wherein said parameter detectable by said gas sensor element includes a concentration of $O_2$.

6. The method of claim 1 wherein said parameter detectable by said gas sensor element includes a concentration of $NO_x$.

7. The method of claim 1 wherein said parameter detectable by said gas sensor element includes a concentration of $NH_3$.

8. The method of claim 1 wherein said parameter detectable by said gas sensor element includes a concentration of $SO_x$.

9. The method of claim 1 wherein said parameter detectable by said gas sensor element includes a concentration of CO.

10. The method of claim 1 wherein said parameter detectable by said gas sensor element includes a concentration of $CO_2$.

11. A gas sensor for use in detecting a parameter of a gas flowing through a flow channel, the gas sensor comprising:
    a gas sensing element;
    a housing coupled or couplable to said flow channel, said housing defining a sensor chamber configured to house said gas sensing element, said housing defining a parallel gas path fluidly coupling said sensor chamber and fluidly coupled or couplable to said flow channel, wherein said parallel gas path provides a gas flow to said sensor chamber from said flow channel based on a pressure differential caused by a velocity of said gas in said flow channel, wherein said parallel gas path extends away from the flow channel for a distance to provide a sufficient friction to soot particles compared to said gas; and
    a plurality of fins disposed on an outer surface of said housing along and adjacent at least part of said parallel gas path, wherein during an operation of said gas sensor, a temperature of said gas in said parallel gas path is reduced by providing cooling of said gas via said plurality of fins.

12. The gas sensor of claim 11 wherein said housing permits said temperature of said gas at said gas sensing element under a steady state to be approximately in a range of 300° C. to 400° C.

13. The gas sensor of claim 12 wherein said temperature of said gas passing through the flow channel is approximately 900° C.

14. The gas sensor of claim 11 wherein said parameter detectable by said gas sensing element includes at least one of a concentration of at least one of the following: $O_2$, $NO_x$, $NH_3$, $SO_x$, CO, or $CO_2$.

* * * * *